United States Patent
Bryant et al.

(10) Patent No.: US 7,083,603 B2
(45) Date of Patent: Aug. 1, 2006

(54) PACKAGING CONFIGURATION AND METHOD FOR PERSONAL CARE ABSORBENT ARTICLES

(75) Inventors: Kristi J. Bryant, Appleton, WI (US); Michelle M. Sroda, Green Bay, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 169 days.

(21) Appl. No.: 10/742,605

(22) Filed: Dec. 19, 2003

(65) Prior Publication Data

US 2005/0137565 A1 Jun. 23, 2005

(51) Int. Cl.
*A61F 13/15* (2006.01)
*A61F 13/20* (2006.01)

(52) U.S. Cl. .................. 604/391; 604/385.05
(58) Field of Classification Search ........... 604/385.05, 604/385.06, 385.02, 385.03, 391, 385.13; 206/440; 24/306, 442, 443, 444, 445, 446, 24/447

See application file for complete search history.

(56) References Cited

U.S. PATENT DOCUMENTS

| | | | |
|---|---|---|---|
| 4,505,704 A * | 3/1985 | Roeder ................. | 604/385.05 |
| 4,556,146 A * | 12/1985 | Swanson et al. ............ | 206/440 |
| 4,598,528 A * | 7/1986 | McFarland et al. ........... | 53/430 |
| 4,680,030 A * | 7/1987 | Coates et al. ................ | 604/391 |
| 4,692,162 A * | 9/1987 | Binker et al. .......... | 604/385.13 |
| 4,770,298 A | 9/1988 | McFarland et al. | |
| 4,772,282 A | 9/1988 | Oakley | |
| 4,775,310 A | 10/1988 | Fischer | |
| 4,776,068 A | 10/1988 | Smirlock et al. | |
| 5,053,028 A * | 10/1991 | Zoia et al. ............. | 604/385.21 |
| 5,300,058 A * | 4/1994 | Goulait et al. .............. | 604/391 |
| 5,318,555 A * | 6/1994 | Siebers et al. .............. | 604/390 |
| 5,392,498 A | 2/1995 | Goulait et al. | |
| 5,565,255 A | 10/1996 | Young et al. | |
| 5,569,230 A * | 10/1996 | Fisher et al. .......... | 604/385.06 |
| 5,595,567 A * | 1/1997 | King et al. ................. | 604/391 |

(Continued)

FOREIGN PATENT DOCUMENTS

EP 0752239 A1 1/1997

(Continued)

OTHER PUBLICATIONS

U.S. Appl. No. 10/732,169.

(Continued)

*Primary Examiner*—Tatyana Zalukaeva
*Assistant Examiner*—Paula L. Craig
(74) *Attorney, Agent, or Firm*—Dority & Manning

(57) ABSTRACT

An absorbent article, such as a feminine care product, includes a liquid permeable top cover, a generally liquid impermeable baffle, and an absorbent structure disposed between the top cover and outer cover. The garment facing side of the baffle includes hook material as a primary attachment mechanism between the baffle and the undergarment. The top cover is a hook compatible material that is releasably attachable to the hook material such that the article can be rolled into a tube-like configuration wherein the hook material is releasably engaged with the hook compatible material for maintaining the article in a rolled configuration. A protective backing sheet is disposed between the top cover and the garment facing side of the baffle in the rolled configuration of the article. The backing sheet has at least one dimension that is less than a corresponding dimension of the article such that a limited portion of the top cover material is releasably engaged by the hook material for maintaining the article in the rolled configuration.

41 Claims, 7 Drawing Sheets

U.S. PATENT DOCUMENTS

| | | | |
|---|---|---|---|
| 5,611,790 A * | 3/1997 | Osborn et al. | 604/391 |
| 5,618,583 A | 4/1997 | Young et al. | |
| 5,676,652 A | 10/1997 | Hunter et al. | |
| 5,713,885 A * | 2/1998 | Jorgenson et al. | 604/385.201 |
| 5,778,457 A * | 7/1998 | Conway | 2/406 |
| 5,876,531 A | 3/1999 | Jacobs et al. | |
| 5,926,926 A * | 7/1999 | Kato | 24/442 |
| 5,961,761 A * | 10/1999 | Heindel et al. | 156/163 |
| 5,964,741 A * | 10/1999 | Moder et al. | 604/358 |
| 5,986,165 A | 11/1999 | Moder et al. | |
| 6,013,062 A | 1/2000 | Dilnik | |
| 6,077,255 A | 6/2000 | Hunter et al. | |
| 6,136,405 A | 10/2000 | Young et al. | |
| 6,163,939 A | 12/2000 | Lacey et al. | |
| 6,174,303 B1 * | 1/2001 | Suprise et al. | 604/385.29 |
| 6,254,582 B1 * | 7/2001 | O'Donnell et al. | 604/385.05 |
| 6,312,417 B1 | 11/2001 | Hansson | |
| 6,363,587 B1 * | 4/2002 | Richter et al. | 24/306 |
| 6,484,371 B1 | 11/2002 | Romanko et al. | |
| 6,579,275 B1 * | 6/2003 | Pozniak et al. | 604/390 |
| 6,582,411 B1 | 6/2003 | Carstens et al. | |
| 6,743,213 B1 * | 6/2004 | Minato | 604/390 |
| 2002/0049420 A1 * | 4/2002 | Suzuki | 604/385.13 |
| 2002/0156448 A1 * | 10/2002 | Steger et al. | 604/385.06 |
| 2003/0065302 A1 * | 4/2003 | Kuroda et al. | 604/385.13 |
| 2005/0124960 A1 * | 6/2005 | Ruman | 604/385.19 |
| 2005/0131376 A1 * | 6/2005 | Wheeler et al. | 604/386 |

FOREIGN PATENT DOCUMENTS

| | | | |
|---|---|---|---|
| EP | 0832631 A2 * | 4/1998 | |
| EP | 0699427 B1 * | 6/1999 | |
| EP | 0752239 B1 | 4/2000 | |
| EP | 1245209 A2 * | 10/2002 | |
| EP | 1279357 A1 * | 1/2003 | |
| EP | 1300125 A2 | 4/2003 | |
| WO | 9507677 | 3/1995 | |
| WO | 9918022 | 4/1999 | |
| WO | 9930659 | 6/1999 | |
| WO | 0037002 | 6/2000 | |
| WO | 0167911 A2 | 9/2001 | |
| WO | 0172254 A2 | 10/2001 | |
| WO | 0172254 A3 | 10/2001 | |

OTHER PUBLICATIONS

U.S. Appl. No. 10/732,907, filed Dec. 10, 2003.

* cited by examiner

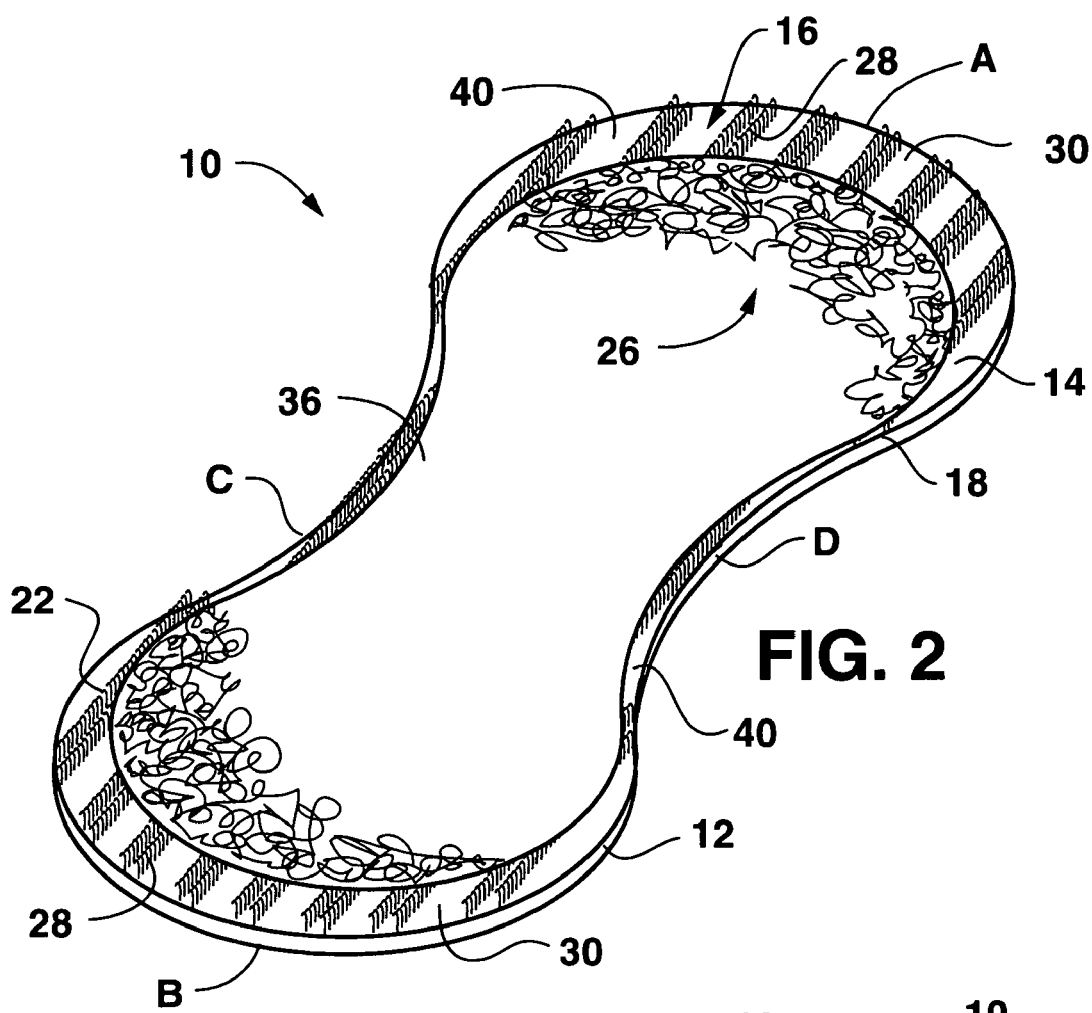
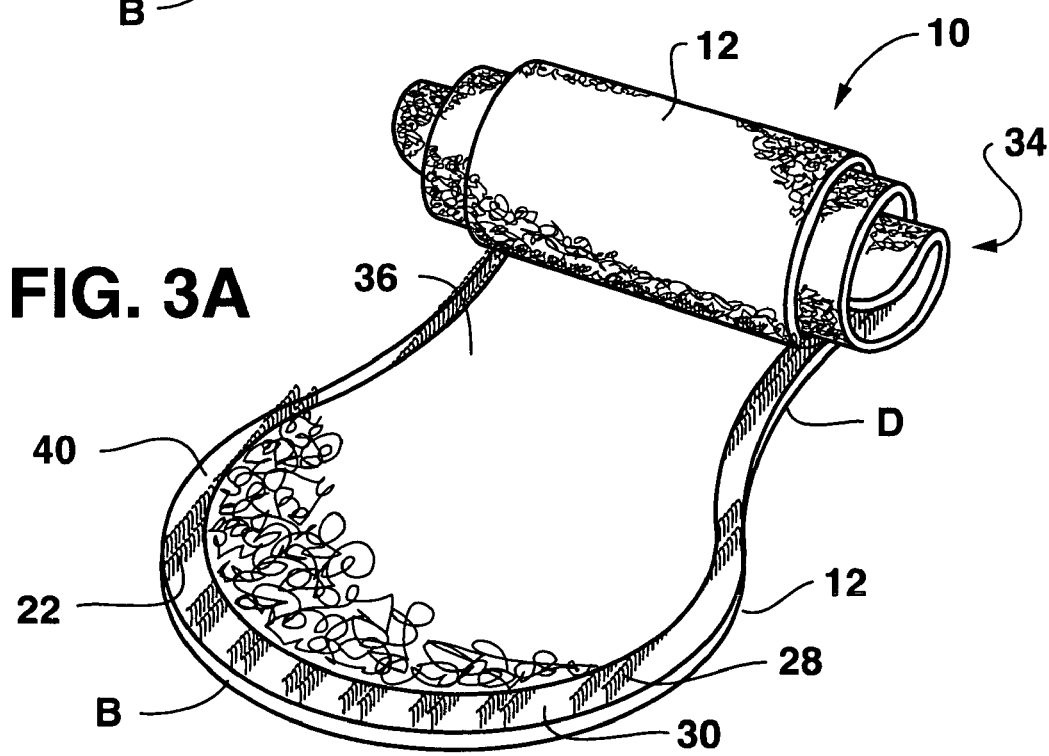

PACKAGING CONFIGURATION AND METHOD FOR PERSONAL CARE ABSORBENT ARTICLES

FIELD OF THE INVENTION

The present invention relates generally to the field of disposable absorbent articles, and more particularly to a method for packaging feminine care articles.

BACKGROUND

Disposable absorbent articles intended to be worn in the crotch portion of an undergarment are well known. The basic form of such absorbent articles typically includes a bodyside liquid-permeable cover, a garment-side liquid-impermeable baffle, and an absorbent core positioned between the cover and the baffle. Such absorbent articles are now in wide use as sanitary napkins, panty shields, panty liners, and adult incontinence pads. While this invention is directed to all such products, for purposes of simplification, the invention will be described with reference to a sanitary napkin.

Present day commercial products have generally performed well, remaining in place and providing the user with ease of placement and removal. Such products typically use an adhesive strip applied to the garment facing side of the baffle for attachment of the article to the wearer's undergarment. The adhesive strip is covered with a peel strip that is removed by the wearer prior to placing the article in the crotch region of the undergarment. These products are typically folded, for example in a tri-fold configuration, and packaged in individual disposable pouches or the like. A number of the pouches are, in turn, packaged in cartons, soft-side packages, and so forth, which are eventually purchased by the consumer. In other commercial embodiments, the peel strip is omitted and the article is attached directly to the pouch or other wrapper material, wherein the combination is then folded into an individual pouch or package. For use, the wearer opens the pouch, peels the article from the pouch material and places the article in the undergarment. The process of packaging the individual articles adds significantly to the overall cost and materials of the articles.

Rolled articles have been discussed in the art as an alternative to traditional folded packaging techniques. The following references describe various such rolled configurations: EP 1 300 125; EP 0 699 427; U.S. Pat. No. 6,254,582; U.S. Pat. No. 5,986,165; U.S. Pat. No. 5,964,741; U.S. Pat. No. 4,772,282; U.S. Pat. No. 4,770,298; U.S. Pat. No. 4,692,162; U.S. Pat. No. 4,598,528; and U.S. Pat. No. 4,505,704.

Additionally, the use of adhesives for attaching the articles may present certain drawbacks. For example, the inner crotch surface of an undergarment, to which these products are typically adhered, is continually being distorted, twisted and stretched due to the dynamics of the wearer. As a result, conventional adhesive attachments can detach causing the undesirable consequence of the sanitary napkin moving out of place. Further, while the sanitary napkin frequently reattaches itself, due to the continuing adhesive nature of the pressure sensitive adhesive, reattachment often places the sanitary napkin in an undesirable position wherein the sanitary napkin does not function properly. Additionally, once the adhesives have been exposed and the article placed into the crotch region of the undergarment, it is generally not practical to remove and reposition the article. In an extreme case, the attachment of the adhesive also results in the adhesive folding over on itself and then becoming unavailable for reattachment.

U.S. Pat. No. 5,300,058 describes a sanitary napkin that does not rely on an adhesive to attach to the undergarment, but instead provides an oriented hook fastening material on the article baffle to secure the article in place. Similarly, U.S. Pat. No. 5,611,790 describes an extensible absorbent article that may use mechanical hook material for securing the article to a garment. U.S. Pat. No. 5,778,457 also describes an absorbent pad utilizing a hook material as the fastening mechanism.

The industry is continually seeking ways to improve feminine care absorbent articles and, in this light, articles that offer an improved attachment mechanism that compliments a more beneficial and economic packaging process would be desirable.

SUMMARY

Objects and advantages of the invention will be set forth in part in the following description, or may be obvious from the description, or may be learned through practice of the invention.

Although the present invention has particular usefulness in the field of feminine care articles such as panty shields or liners and sanitary napkins, it should be appreciated that any manner of personal care absorbent article may benefit from the invention, including incontinence articles, and the like. All such uses are within the scope and spirit of the invention. For ease of description only, the working environment of the invention is assumed to be feminine care sanitary napkins.

The invention relates to a unique absorbent article configuration that allows the article to be rolled into a compact and discrete configuration prior to use. The article includes conventional features such as a generally liquid permeable top cover, a generally liquid impermeable and vapor permeable outer cover or baffle, and an absorbent structure disposed between the top cover and baffle. The baffle includes hook material defined in a pattern on the garment facing side thereof, and the top cover is a hook compatible material, such as a nonwoven material. Thus, the opposite sides of the article releasably engage with each other and the article is easily rolled and maintained in its rolled configuration without the need for additional retaining means, such as adhesives, ties, tabs, or the like, by a minimal degree of releasable engagement between the top cover and the baffle. The substantial portion of the top cover is protected from engagement with the hook material on the baffle in the rolled configuration of the article by a protective backing sheet. For use, a wearer simply unrolls the article, removes the backing sheet, and attaches the baffle side of the article directly to the undergarment without the use of adhesives.

Articles according to the invention also provide a means to discretely dispose of soiled articles without the need for disposal wrappers, pouches, or the like. After removing the article from the undergarment, the wearer can simply roll the product up with the baffle side outwardly facing. The soiled top cover is thus not visible and the article will hold this rolled configuration without additional adhesives or the like for subsequent disposal. If desired, the protective backing sheet from a new article may be used to wrap the soiled article prior to disposal.

Once rolled, the articles may be directly packaged in any conventional packaging materials. Alternatively, the rolled articles may be individually wrapped with conventional wrapping materials prior to being packaged.

The article utilizes unique placement of hook-type attachment material in a pattern on the garment facing side of the baffle for the purposes of attaching the baffle directly to the undergarment without additional attachment devices, and for holding the article in its rolled tube-like configuration by releasably engaging with a limited exposed portion of the top cover sheet material.

The pattern of hook material defined on the baffle may be any desired continuous or discontinuous placement pattern, for example stripes, dashes, swirls, dots or island-like regions, etc. The amount and pattern of the hook material should be sufficient to ensure that the baffle remains secured in the crotch region of the undergarment yet does not render the baffle vapor impermeable. In a desirable embodiment, the garment facing side of the baffle presents an overall uniform pattern of hook material generally over its entire surface area such that a uniform vapor permeability gradient is established. For example, the vapor permeability gradient of a transverse section of the article at one longitudinal end is generally the same for a comparable transverse section in the medial or opposite longitudinal end of the article. The garment will thus be retained in the undergarment more securely than if a single area or region of conventional adhesive were used, such as a longitudinal strip of adhesive along the center of the baffle as with many types of commercial articles. Yet, even with such improved attachment, the article is remains breathable and is easily removable and variably positionable as required by the wearer.

In a particular embodiment, the pattern may be defined by stripes of the hook material having a width of about one-half of a distance between adjacent stripes. The stripes may be, for example, about one-eight inch and spaced apart about one-fourth inch. The regions of hook material in the patterns may be about 5% to about 75% of a total surface area of the garment facing side of the baffle. In a particular embodiment, the hook material may be between about 25% to about 50% of the total surface area such that at least about 50% of the baffle remains breathable.

The degree of engagement of the hook material with the top cover in the rolled configuration should not result in appreciable damage to the top cover material. Although unfastening of the hook material from the top cover material would in all likelihood not damage the functionality of the top cover, it may be perceived by certain consumers that resulting piling on the top cover from such attachment indicates an inferior product or may cause skin irritation. In this regard, the configuration according to the present invention includes the protective backing sheet disposed to protect the substantial portion of the top cover from engagement with the hook material on the garment facing side of the baffle. The backing sheet may be generally the same size and overall configuration as the baffle and top cover with at least one dimension that is less than a corresponding dimension of the top cover and/or baffle. For example, the backing sheet may be narrower in a lateral direction, or shorter in a longitudinal direction as compared to the overall shape of the article. Alternately, the backing sheet may be of a size and shape so as to define an exposed border region when placed adjacent the top cover or baffle. In this manner, regardless of whether the protective backing sheet is placed against the top cover or against the garment facing side of the baffle prior to rolling, a relatively small portion of the top cover hook compatible material is releasably engaged by the hook material in the rolled configuration of the product.

It should be appreciated that the degree of attachment of the top cover (or area not covered by the protective backing sheet) depends on the desired degree of engagement with the hook material to ensure that the article is maintained in its rolled configuration during packaging, shipping, handling, and generally at all times prior t use. Although the amount may vary, generally between 75% to about 95% of the surface area of said top cover is protected by said backing sheet from engagement with the hook material. Coverage amounts beyond this range are also within the scope and spirit of the invention.

In a particular embodiment, the protective backing sheet is a hook compatible material, such as a nonwoven material, and is disposed against the garment facing side of the baffle prior to rolling the article. The backing sheet will thus readily attach to the hook material and maintain its position during the rolling process. For use, the consumer simply unrolls the article, detaches the protective backing sheet, and places the article in a desired position in the undergarment.

In an alternate embodiment, the protective backing sheet may be a poly or film material that does not attach to the hook material. This embodiment renders removal of the backing sheet essentially noise-free, a feature that may be desirable to consumers. The poly or film material may be placed against either the top cover or the baffle prior to rolling the article.

In a particular embodiment, the protective backing sheet is shorter than the article in a longitudinal direction and is disposed such that a single longitudinal edge portion of the top cover or baffle is exposed for engagement in the rolled configuration of the article. The article is rolled from the opposite longitudinal end towards the longitudinal end having the exposed portion. The protective backing sheet may be disposed against the top cover or against the garment facing side of the baffle prior to rolling. The result is the same in either embodiment.

In an alternate embodiment, the article is rolled from one lateral side towards an opposite lateral side. In this embodiment, an exposed lateral side region of the garment facing side of the baffle or the top cover (depending on placement of the protective backing sheet) is provided for limited engagement of the top cover and hook material in the rolled configuration of the article.

The degree or relative amount of attachment between the top cover and the hook material on the garment facing side of the baffle may also be determined as a function of peel resistance. There is a desirable range of engagement that may be empirically determined depending on the shape and type of the hooks, type of cover material, shape of the absorbent article, and so forth. Peel values of less than 500 g are generally desired. Engagement with peel values between about 50 g to about 100 g should result in little or no damage to conventional nonwoven cover sheet materials.

The hook material may be deposited on the baffle by conventional methods, including by applying strips of hook material tape with adhesive, etc. In a particularly desirable embodiment, the hook material is extruded and laminated directly onto a base material used for the baffle, as described in greater detail below.

If desired, an additional absorbent device, such as a tampon or interlabial device, may be placed in the article and rolled therewith such that the article is essentially wrapped around the additional device. In this way, the wearer is presented with two devices (if needed) in single compact rolled configuration.

The invention also encompasses absorbent articles as described herein that are capable of being rolled and packaged in such rolled configuration.

Additionally, the invention encompasses a method for rolling uniquely formed absorbent articles into a compact tube-like configuration for packaging.

Aspects of the invention will described below in greater detail by reference to particular embodiments, examples of which are illustrated in the figures.

BRIEF DESCRIPTION OF THE FIGURES

FIG. 2 is a perspective view of the absorbent article according to FIG. 1 with the backing sheet placed against the baffle.

FIG. 3A is a perspective view of the absorbent article according to FIG. 2 being rolled from one longitudinal end to the other.

DETAILED DESCRIPTION

Figure 1:
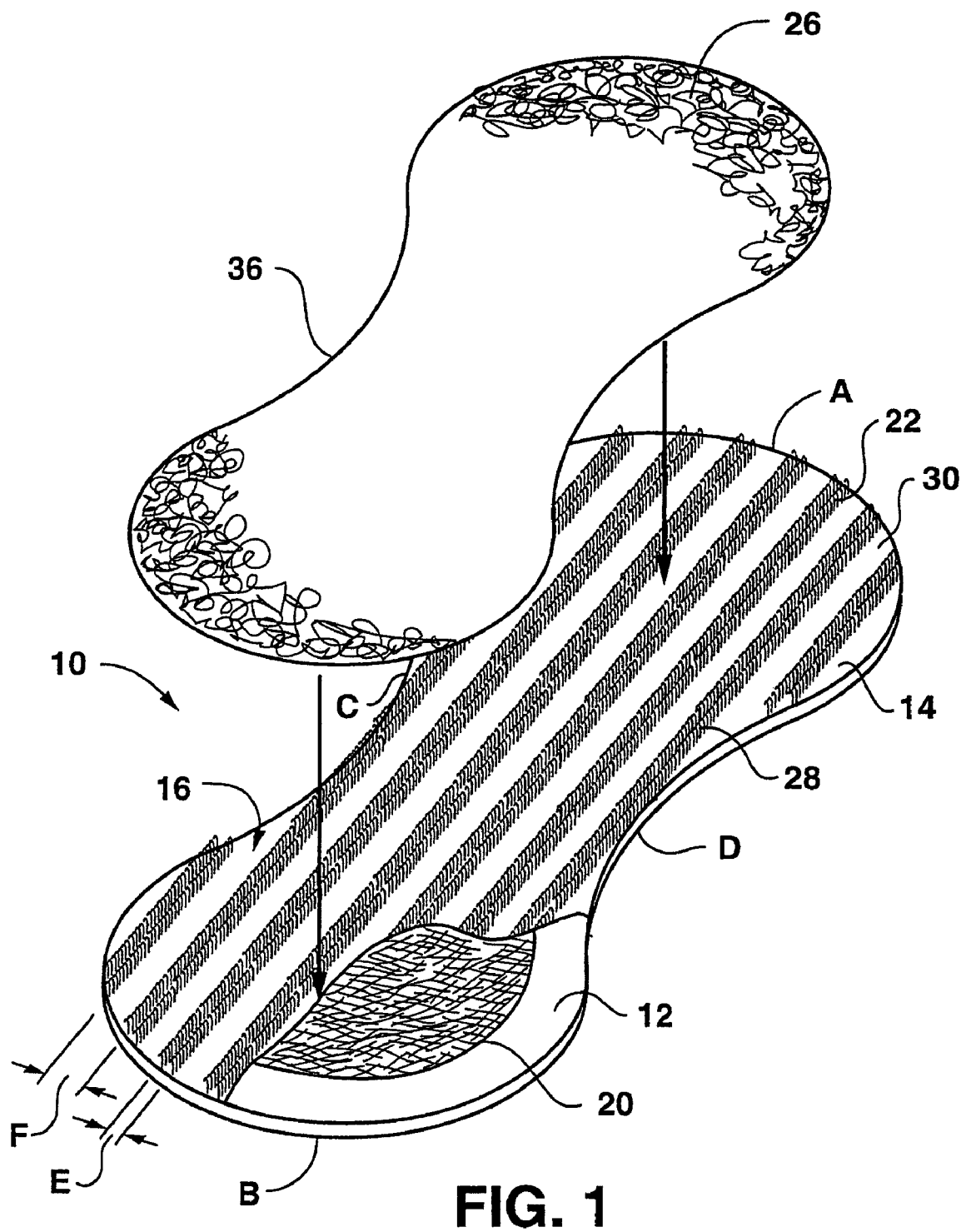
FIG. 1 is a perspective partial cut-away view of an absorbent article according to the invention with the backing sheet removed.

The invention will now be described in detail with reference to particular embodiments thereof. The embodiments are provided by way of explanation of the invention, and are not meant as a limitation of the invention. For example, features described or illustrated as part of one embodiment may be used with another embodiment to yield still a further embodiment. It is intended that the present invention include these and other modifications and variations as come within the scope and spirit of the invention.

Referring to the Figures, in which like numerals indicate like parts throughout the several views, embodiments of a disposable absorbent article 10 are depicted. For purposes of illustration only, the disposable absorbent article 10 is exemplified as a sanitary napkin. Typically, a sanitary napkin is worn by a female to absorb body fluids, such as menses, blood, urine and other body excrements discharged during a menstrual period. Although the invention has particular usefulness for feminine care articles and, it should be appreciated that the invention is in no way limited to sanitary napkins in particular, or to feminine care articles in general. One skilled in the art will readily understand the adaptability of the invention to other personal care and health care articles, such as, for example, panty liners, adult incontinence garments and the like that attach to a wearer's undergarment.

The term "disposable", as used herein, means that the absorbent article is discarded after a single use and is not intended to be laundered for subsequent reuse.

Referring to the figures in general, the absorbent article 10 according to the invention includes a generally liquid permeable top cover 12, a generally liquid impermeable and vapor permeable outer cover or baffle 14, and an absorbent structure 20 disposed between the top cover 12 and baffle 14. The top cover 12 and baffle 14 may be sealed together at their peripheral edges utilizing known techniques, such as, for example, gluing, crimping, hot-sealing or the like. The article 10 may take on various shapes, but will generally have opposite longitudinal ends A, B and lateral sides C, D. In the illustrated embodiments, the article 10 has a well-known hourglass shape. Various other geometries of absorbent articles, including feminine care articles, are well known to those skilled in the art, and all such embodiments are within the scope and spirit of the invention.

The absorbent article 10 is desirably provided with sufficient capacity to absorb and retain the intended amount and type of bodily exudate(s). The absorbent capacity is provided by the fluid retentive absorbent structure or web 20. The absorbent structure 20 can be any structure or combination of components which are generally compressible, conformable, non-irritating to a wearer's skin, and capable of absorbing and retaining liquids and certain body wastes. For example, the structure 20 may include an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In a particular embodiment, the absorbent web material is a matrix of cellulosic fluff, and may also include superabsorbent hydrogel-forming particles. The cellulosic fluff may comprise a blend of wood pulp fluff. One preferred type of fluff is identified with the trade designation NB 416, available from Weyerhaeuser Corp., and is a bleached, highly absorbent wood pulp containing primarily soft wood fibers. The absorbent materials may be formed into a web structure by employing various conventional methods and techniques. For example, the absorbent web may be formed with a dry-forming technique, an air forming technique, a wet-forming technique, a foam-forming technique, or the like, as well as combinations thereof. Methods and apparatus for carrying out such techniques are well known in the art.

The absorbent structure 20 can contain superabsorbent materials which are effective in retaining body fluids. As a general rule, the superabsorbent material is present in the absorbent web in an amount of from about 0 to about 90 weight percent based on total weight of the web. Superabsorbents have the ability to absorb a large amount of fluid in relation to their own weight. Typical Superabsorbents used in absorbent articles, such as sanitary napkins, can absorb anywhere from 5 to 60 times their weight in body fluids. Superabsorbent materials are well known in the art and can be selected from natural, synthetic, and modified natural polymers and materials.

The absorbent web material may also be a coform material. The term "coform material" generally refers to composite materials comprising a mixture or stabilized matrix of thermoplastic fibers and a second non-thermoplastic material. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein in their entirety by reference thereto for all purposes.

The absorbent web material utilized in the absorbent structure 20 is also selected so that the individual absorbent structure possesses a particular individual total absorbency depending on the intended article of use. For example, for infant care products, the total absorbency can be within the range of about 200–900 grams of 0.9 wt % saline, and can typically be about 500 g of saline. For adult care products, the total absorbency can be within the range of about 400–2000 grams of saline, and can typically be about 1300 g of saline. For feminine care products, the total absorbency can be within the range of about 7–50 grams of menstrual fluid, and can typically be within the range of about 30–40 g of menstrual fluid.

The absorbent structure 20 may be a multi-component and may include, for example, an intake layer or transfer delay layer in combination with the underlying absorbent web. Such configurations are well known to those skilled in the art.

The fluid permeable top cover 12 has an outwardly facing surface that may contact the body of the wearer and receive bodily exudate(s). The top cover 12 desirably is made of a material which is flexible and non-irritating to the wearer. As used herein, the term "flexible" is intended to refer to materials which are compliant and readily conform to the bodily surface(s) with which such materials are in contact, or materials which respond by easily deforming in the presence of external forces.

The top cover 12 is provided for comfort and conformability and functions to direct bodily exudate(s) away from the body, through the top cover 12 and toward the absorbent structure 20. The top cover 12 should retain little or no liquid in its structure so that the cover provides a relatively comfortable and non-irritating surface next to the tissues within the vestibule of a female wearer. The top cover 12 can be constructed of any woven or nonwoven material which is easily penetrated by bodily fluids which contact the surface of the cover. Examples of suitable cover materials include rayon, bonded carded webs of polyester, polypropylene, polyethylene, nylon, or other heat-bondable fibers, polyolefins, such as copolymers of polypropylene and polyethylene, linear low-density polyethylene, and aliphatic esters such as polylactic acid. Finely perforated film webs and net material can also be used. The cover may be apertured to increase its fluid intake capacity. A specific example of a suitable cover material is a bonded carded web made of polypropylene and polyethylene such as that used as cover stock for KOTEX® pantiliners and obtainable from Sandler Corporation, Germany. Other examples of suitable materials are composite materials of polymer and nonwoven fabric materials. The composite materials are typically in the form of integral sheets generally formed by the extrusion of a polymer onto a web of spunbonded material. The fluid permeable cover 12 can also contain a plurality of apertures formed therein which are intended to increase the rate at which bodily fluid(s) can penetrate through the cover and into the absorbent structure 20.

The top cover 12 may also be embossed with any desired embossing pattern to define embossed channels. Embossing techniques are well known to those skilled in the art. An embossing pattern not only creates an aesthetically pleasing surface, the channels facilitate intake of menses fluid. Menses will tend to flow along the densified edges of the channels rather than pool on contact points of the top cover 12.

The top cover 12 can be maintained in secured relation with the absorbent structure 20 by bonding all or a portion of the adjacent surfaces to one another. A variety of bonding methods known to one of skill in the art can be utilized to achieve any such secured relationship. Examples of such methods include, but are not limited to, the application of adhesives in a variety of patterns between the two adjoining surfaces, entangling at least portions of the adjacent surface of the absorbent with portions of the adjacent surface of the cover, or fusing at least portions of the adjacent surface of the cover to portions of the adjacent surface of the absorbent.

The baffle 14 has an outer garment facing side 16 and may be any one of a number of suitable liquid impermeable materials known in the art for use as outer covers or baffles in absorbent articles. Preferably, the baffle 14 will permit the passage of air and moisture vapor out of the article 10 while blocking the passage of body fluids. A suitable material is a micro-embossed polymeric film, such as polyethylene or polypropylene, having a thickness of about 0.025 to 0.13 millimeters. Bicomponent films can also be used, as well as woven and nonwoven fabrics which have been treated to render them liquid impermeable. A specific example of a baffle material is a polyethylene film such as that used in KOTEX® pantiliners and obtainable from Pliant Corporation, Schaumburg, Ill., USA. The cover can be maintained in secured relation with the absorbent structure 20 by bonding all or a portion of the adjacent surfaces to one another. A variety of bonding methods known to one of skill in the art can be utilized to achieve any such secured relation. Examples of such methods include, but are not limited to, ultrasonic bonding, thermal bonding, or the application of adhesive materials in a variety of patterns between the two adjoining surfaces.

Although not illustrated in the figures, it should be understood that the article 10 may include laterally extending wings that aid in securing the article 10 to the wearer's undergarment. Such wings are well known in the art and generally function by folding around the edges of the undergarment crotch region and attaching to each other.

A hook material 22 is provided in a pattern on the garment facing side 16 of the baffle 14. The hook material 22 is defined in a suitable pattern desirably over substantially the entire surface of the garment facing side 16. The particular design, shape, etc., of the pattern are not limiting features. The pattern should provide sufficient coverage of hook material 22 to ensure reliable attachment of the article 10 to the wearer's undergarment without unnecessarily the vapor permeability characteristic of the baffle material. Undergarments are typically made from various woven or non-woven materials that present an attachment surface for conventional hook materials. Thus, the hook material 22 on the garment facing side 16 of the baffle 14 may attach directly to the inner or body facing side of wearer's undergarment, and can provide the primary attachment mechanism between the article 10 and the garment.

The amount of the hook material 22 relative to the entire surface area of the body facing side 16 may vary between about 5% to about 75%, with desirable coverage being about 10% to about 50% of the surface area. In a particular embodiment, the coverage is about 25%. Desirably, the amount of coverage of the hook material 22 should be such that at least about 50% of the baffle 14 is not covered by hook material and remains vapor permeable.

As mentioned, the pattern of the hook material 22 may vary, but is desirably defined by deposits of hook material 22 interspaced with "bare" uncovered regions 30 of the base baffle material 14. For example, the hook material may be defined by generally longitudinally deposited continuous or discontinuous regions interspaced with uncovered regions 30. In this way, the vapor permeability profile of the baffle 14 is generally uniform over the surface area of the baffle 14 such that the permeability of a random transverse section of the article is generally uniform over the length of the article. It should be appreciated, however, that laterally oriented deposits of the hook material extending generally between laterals sides C and D are also within the scope and spirit of the invention.

In a particular embodiment illustrated in FIGS. 1 through 8, the hook material 22 is defined in a pattern of continuous longitudinal stripes 28 having a width E (FIG. 1) of, for example, about one-eight of an inch. The stripes 28 are interspaced with bands 30 of the bare baffle material 14 having a width F of, for example, one-quarter of an inch. Thus, the surface area of the hook material 22 is about one-half of that of the bare baffle regions 30 of baffle material.

In an alternate embodiment, the pattern of hook material 22 may be defined in different complementary patterns. For example, in the embodiment of FIG. 9, the hook material 22 is defined in a pattern of discontinuous deposits, such as the illustrated pattern of broken stripes or alternating "dashes" 32. The discontinuous deposits may be, for example, island-like deposits such as circles, dots, etc., or deposits of irregular shapes. It should be appreciated that any desired pattern or shape of hook material deposits are within the scope and spirit of the invention.

The hook material 22 essentially constitutes the male component of conventional hook-and-loop mechanical fastening systems that cooperates with a "loop" or loop-like material of the wearer's undergarment to define a releasable and re-attachable fastening system. Any number of commercially available and conventional micro-hook materials used in absorbent articles, including diaper attachment tabs, etc., may be used in the present invention. Conventional systems are, for example, available under the VELCRO® trademark. The hook element may be provided by a single-prong hook configuration, a multiple-prong hook configuration or by a generally continuous, expanded-head configuration, such as provided by a mushroom-head type of hook element. The many arrangements and variations of such fastener systems are collectively known in the art as hook-and-loop fasteners.

Examples of hook-and-loop fastening systems and components are described in U.S. Pat. No. 5,019,073 issued May 28, 1991 to T. Roessler et al., the entire disclosure of which is hereby incorporated by reference in a manner that is consistent herewith. Other examples of hook-and-loop fastening systems are described in U.S. patent application Ser. No. 366,080 entitled HIGH-PEEL TAB FASTENER, filed Dec. 28, 1994 by G. Zehner et al. which corresponds to U.S. Pat. No. 5,605,735; and U.S. patent application Ser. No. 421,640 entitled MULTI-ATTACHMENT FASTENING SYSTEM, filed Apr. 13, 1995 by P. VanGompel et al.; the entire disclosures of which are hereby incorporated by reference in a manner that is consistent herewith. Examples of fastening tabs constructed with a carrier layer are described in U.S. patent application Ser. No. 08/603,477 of A. Long et al., entitled MECHANICAL FASTENING SYSTEM WITH GRIP TAB and filed Mar. 6, 1996 which corresponds to U.S. Pat. No. 5,624,429 which issued Apr. 29, 1997, the entire disclosure of which is hereby incorporated by reference in a manner which is consistent herewith.

In a particularly desirable embodiment of the invention, the hook material 22 is directly extruded onto the base baffle material 14 to define laminated regions of the hook material 22 integral with the baffle material 14. Processes for directly extruding regions of a hook material directly onto a base material are described, for example, in U.S. Pat. Nos. 5,518,795; 5,260,015; and 5,744,080, all from Velcro Industries B.V. and incorporated herein in their entirety for all purposes. The extrusion process described in these patents may be used to directly deposit or embed the hook material 22 with the baffle material 14 in any desired pattern. The baffle material 14 is selected so as to be suitable for the extrusion process and to support the embedded hook material 22. From a manufacturing perspective, rolls of the baffle material 14 having the hook material already embedded therein may be supplied directly into an in-line processing line for producing the articles 10. The extruded embedded regions of hook material 22 also have a reduced thickness as compared to the hooked regions of conventional hook tape adhered to a base material.

The top cover 12 is made of a material that is "hook compatible" with the hook material 22 on the baffle 14 and, thus, is releasably attachable to the baffle 14 when the article 10 is rolled in accordance with the invention. "Hook-compatible" material should be understood to encompass any material functioning as a loop or loop-like surface for releasable attachment with the hook material 22. Suitable materials include, for example, a woven fabric, a nonwoven fabric, a knitted fabric, a perforated or apertured layer, and the like, as well as combinations thereof. Any number and combination of suitable cover materials may provide the "hook compatible" feature.

As seen, for example, in FIGS. 3A, 3B, 3C, 5A, and 5B, the unique configuration of the article 10 according to the invention allows the article to be configured into a compact and discrete spiral or tube-like configuration 34 prior to use. The configuring of the article can include folding, rolling or the like, as well as combinations thereof. Because the top cover 12 and baffle 14 are releasably attachable, as described above, the article 10 is easily rolled and maintained in the rolled configuration with a minimal degree of releasable engagement between the top cover 12 and baffle 14 without the need for additional retaining means, such as adhesives, ties, tabs, or the like. The substantial portion of the top cover 12 is protected from engagement with the hook material 22 in the rolled configuration 34 by a protective backing sheet 36 placed between the top cover 12 and baffle 14, as discussed in greater detail below. For use, the wearer simply unrolls the article 10, removes the backing sheet 36, and attaches the baffle 14 directly to their undergarment by way of the hook material 22 provided on the garment facing side 16 of the baffle 14.

By limiting the degree of engagement of the hook material 22 with the cover 12, the backing sheet 36 protects the top cover 12 from any appreciable or perceived damage. As discussed, although unfastening of the hook material 22 from the top cover material 12 would in all likelihood not damage the functionality of the top cover 12, it may be perceived by certain consumers that resulting piling on the top cover 12 from such attachment indicates an inferior product or may cause skin irritation. In this regard, the configuration according to the present invention includes the protective backing sheet 36 disposed to protect the substantial portion of the top cover 12 from engagement with the hook material 22 on the garment facing side of the baffle.

Figure 4:
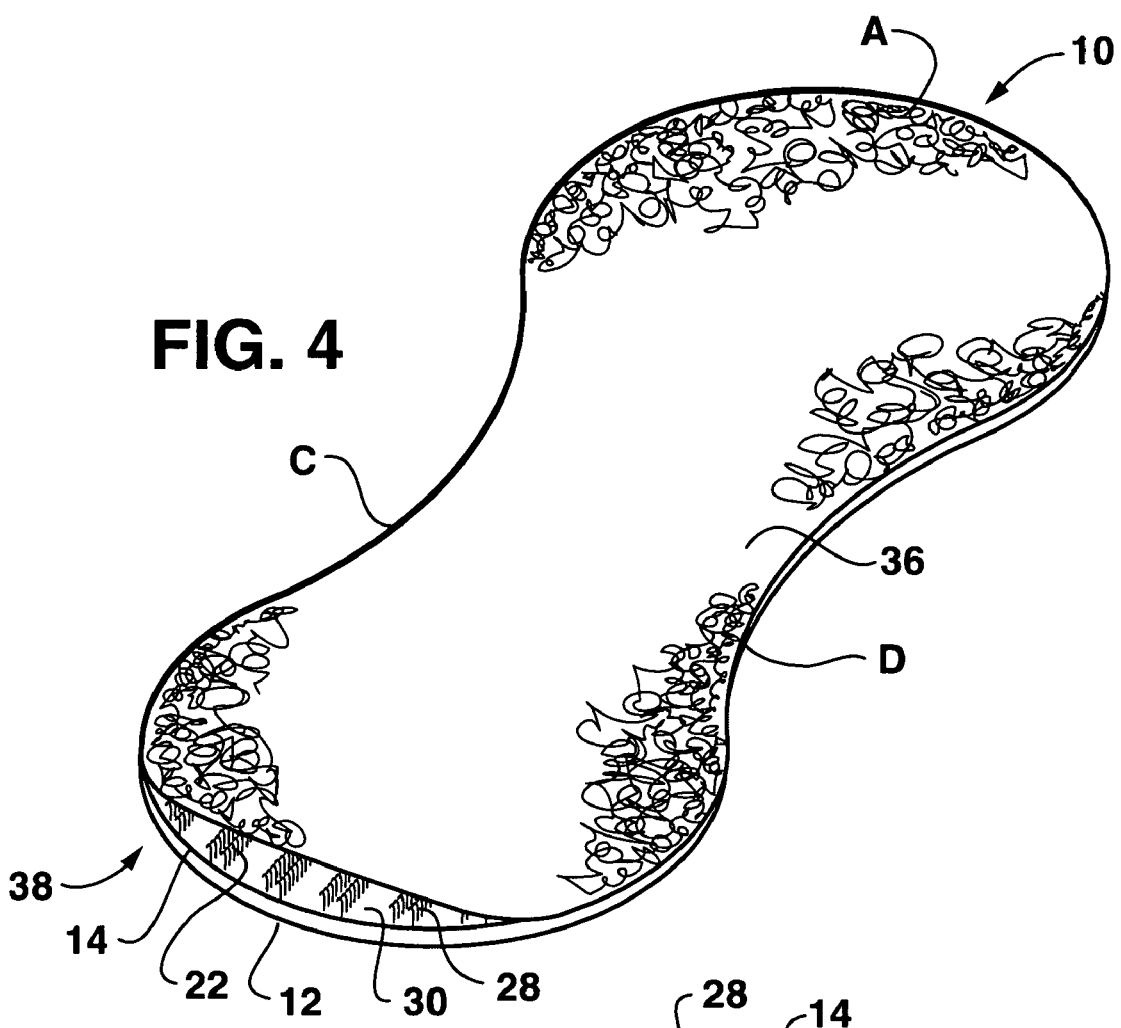
FIG. 4 is a perspective view of an alternate embodiment of an article according to the invention.
Figure 5A:
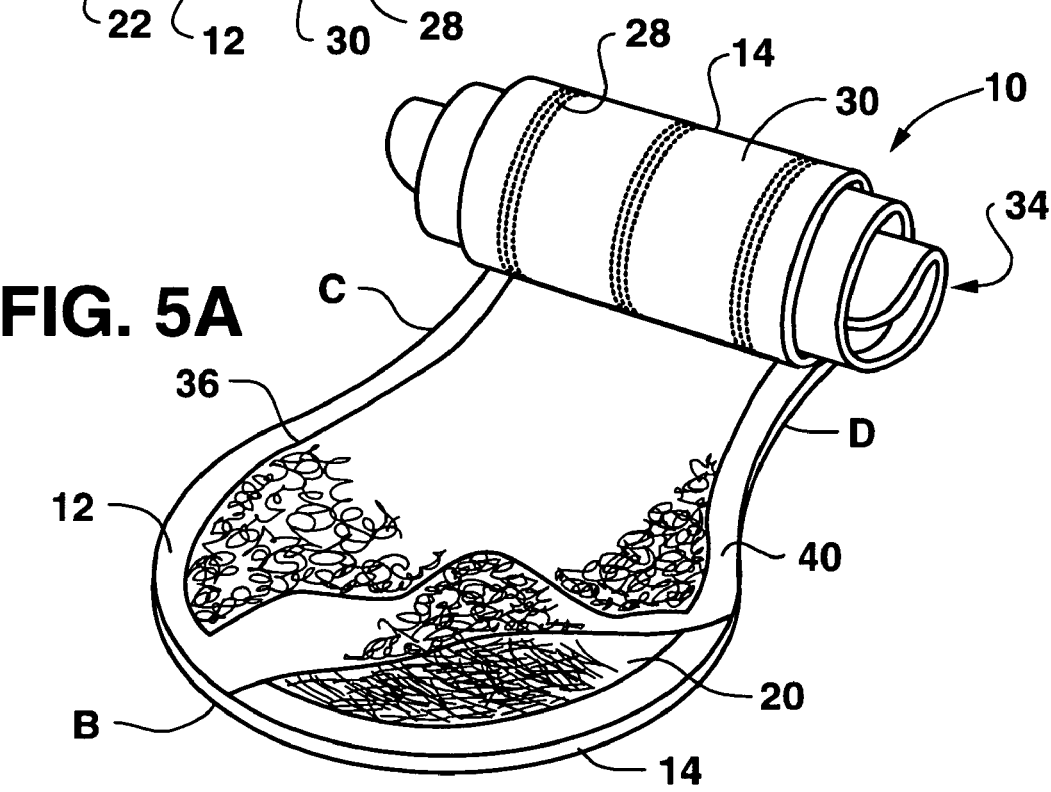
FIG. 5A is a perspective and partial cut-away vies of an alternate embodiment being rolled from one longitudinal end to the other.
Figure 9:
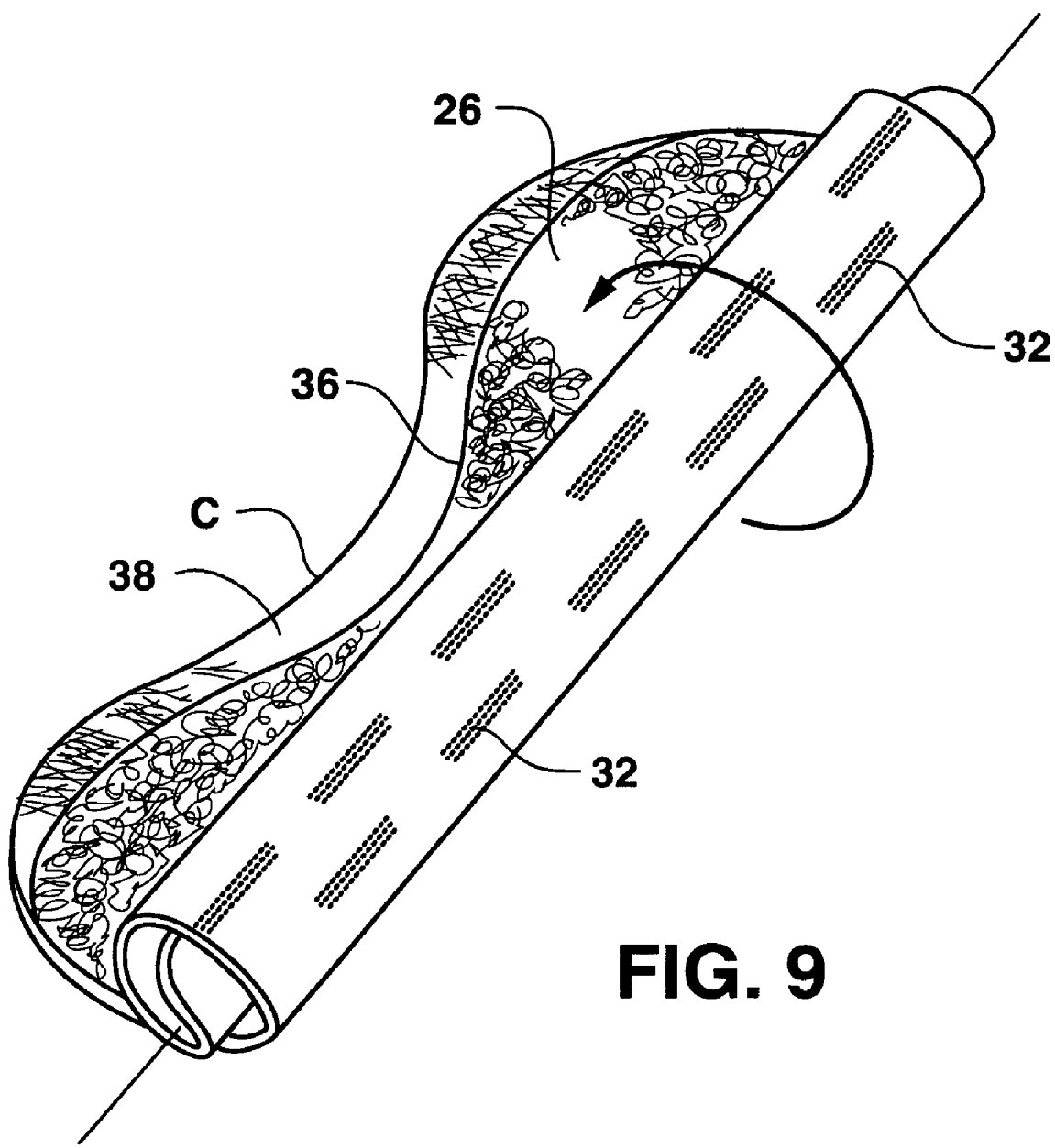
FIG. 9 is a perspective view of an alternate embodiment of the article being rolled from one lateral side thereof to the other lateral side.

The backing sheet 36 may be formed of various suitable materials and take on any desired shape. For example, as illustrated in the various figures, the baking sheet 36 may have generally the same size and overall configuration as the baffle 14 and top cover 12 with at least one dimension that is less than a corresponding dimension of the top cover and/or baffle to provide the minimal degree of attachment between the hook material 22 and top cover 12 in the rolled configuration of the article 10. For example, the backing sheet 36 may be narrower in a lateral direction, as seen in FIG. 9, to expose a single lateral-side border 38 of the top cover 12 or baffle 14 (depending on initial placement of the backing sheet 36). Alternately, the backing sheet 36 may be shorter in a longitudinal direction, as seen in FIG. 4, compared to the overall shape of the article to define a single longitudinal-end border 38. In still an alternate embodiment as seen in FIGS. 2, 3a, and 5A, the backing sheet 36 may be of a size and shape so as to define an exposed overall border region 40 when placed adjacent the top cover 12 or baffle 14. In all embodiments, regardless of whether the protective backing sheet 36 is placed against the top cover 12 or against the garment facing side 16 of the baffle 14 prior to rolling the article, a relatively small portion of the top cover hook compatible material is releasably engaged by the hook material 22 in the rolled configuration 34 of the product.

It should be appreciated that the degree of attachment of the top cover 12 (area not covered by the protective backing sheet 36) depends on the desired degree of engagement with the hook material 22 to ensure that the article is maintained in its rolled configuration 34 during packaging, shipping, handling, and generally at all times prior t use. Although the amount may vary, generally between 75% to about 95% of the surface area of said top cover 12 is protected by the backing sheet 36 from engagement with the hook material 22. Coverage amounts beyond this range are also within the scope and spirit of the invention.

In particular embodiments, the protective backing sheet 36 is a hook compatible material, such as a nonwoven material 26, and may be disposed against the garment facing side 16 of the baffle 14 prior to rolling the article, as depicted in FIGS. 1 through 4. The backing sheet 36 will thus readily attach to the hook material 22 and maintain its position during the rolling process. For use, the consumer simply unrolls the article 10, pulls the protective backing sheet 36 from the baffle 14, and presses the garment facing side 16 of the baffle with exposed hook material 22 directly against the crotch region of the undergarment.

Figure 6:
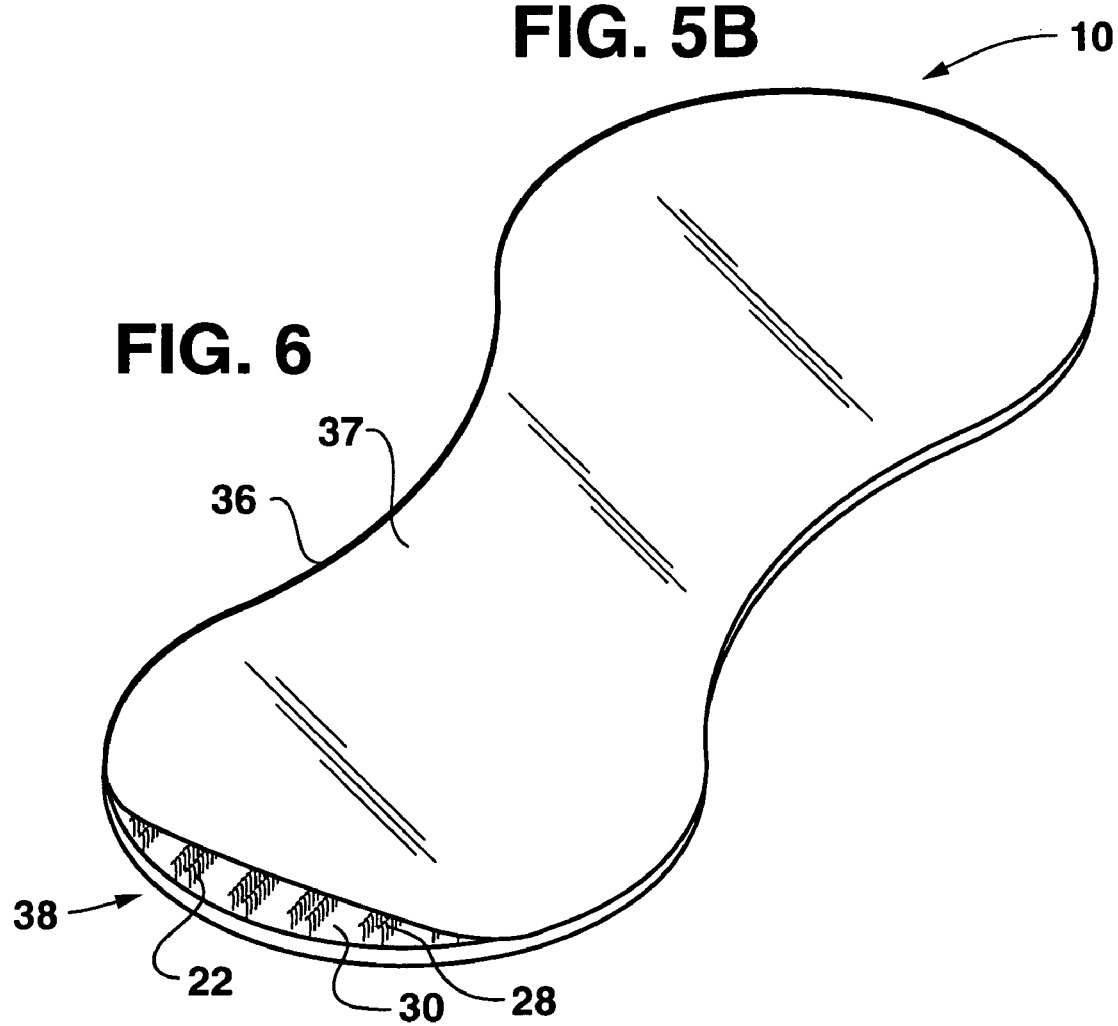
FIG. 6 is a perspective view of an alternate embodiment utilizing a film backing sheet material.

In an alternate embodiment, the protective backing sheet 36 may be a poly or film material 37, as depicted in FIG. 6, that does not attach to the hook material 22 yet protects the tope cover 12. This embodiment renders removal of the backing sheet essentially noise-free, a feature that may be desirable to consumers. The poly or film material may be placed against either the top cover 12 or the baffle 14 prior to rolling the article.

The degree or relative amount of attachment between the top cover 12 and the hook material 22 on the garment facing side 16 of the baffle 14 may also be determined as a function of peel resistance. There is a desirable range of engagement that may be empirically determined depending on the shape and type of the hooks, type of cover material, shape of the absorbent article, and so forth. Peel values of less than 500 g are generally desired. Engagement with peel values between about 50 g to about 100 g should result in little or no damage to conventional nonwoven cover sheet materials. The degree of engagement between a hook-compatible backing sheet 36 and the baffle 14 may also be determined as a function of peel resistance. Although damage to the backing sheet is not a concern, the backing sheet should not be difficult for a consumer to remove.

It should be appreciated that the articles 10 can be rolled in various ways. For example, referring to FIGS. 3A and 5A, the article 10 is rolled from longitudinal end A towards the opposite longitudinal end B such that the resulting rolled configuration has a transverse axis. Alternatively, as illustrated in FIG. 9, the article 10 may be rolled from a lateral side D (FIG. 1) towards the opposite lateral side C such that the resulting rolled article 10 has a longitudinally extending roll axis.

Figure 3B:
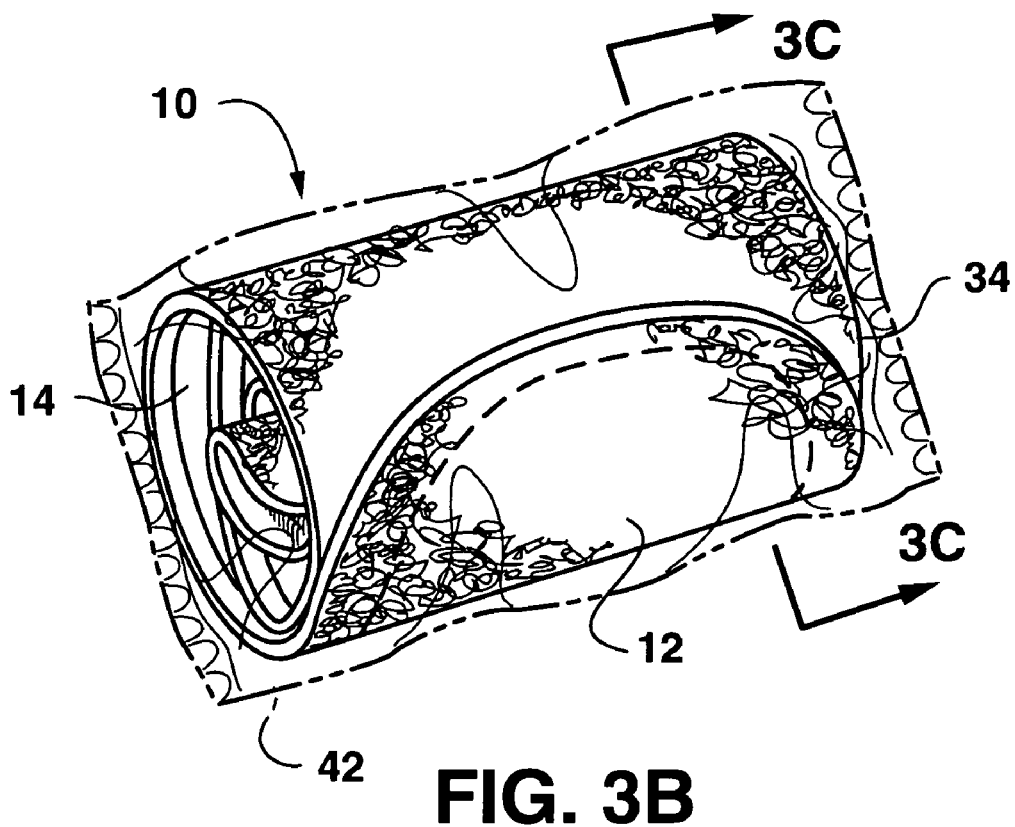
FIG. 3B is a perspective view of the article of FIG. 3A after being rolled and wrapped in an individual wrapper.
Figure 3C:
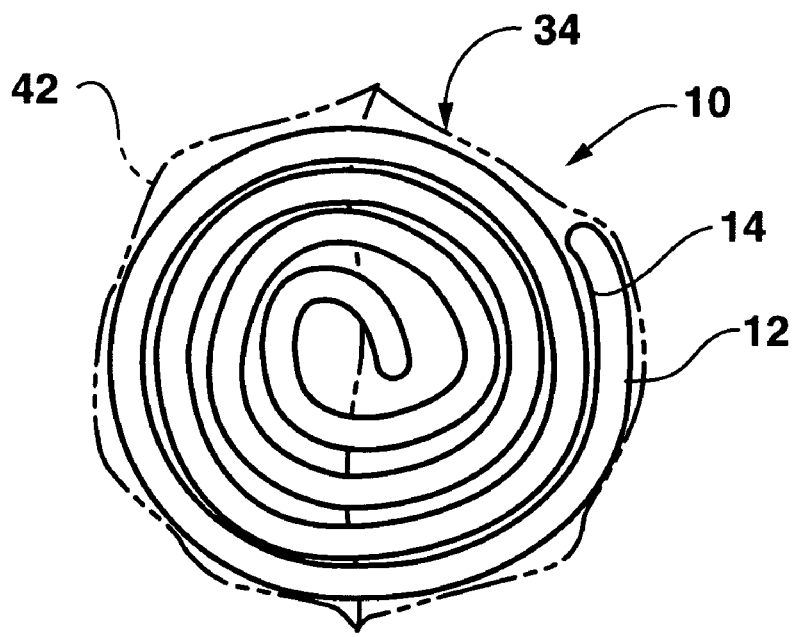
FIG. 3C is a cross-sectional view of the article of FIG. 3B taken along the lines indicated in FIG. 3B.

As seen in FIGS. 3A and 3B, the articles 10 may be rolled such that the top cover 12 is outwardly facing. In these embodiments, the backing sheet 36 is placed against the baffle 14 and the article is rolled in the direction depicted in FIG. 3A. In an alternate embodiment, the articles 10 may be rolled such that the baffle 14 is outwardly facing, such as in FIGS. 5A, 5B, and 9. This orientation may be desirable to protect and keep the top cover 12 clean.

Figure 7:
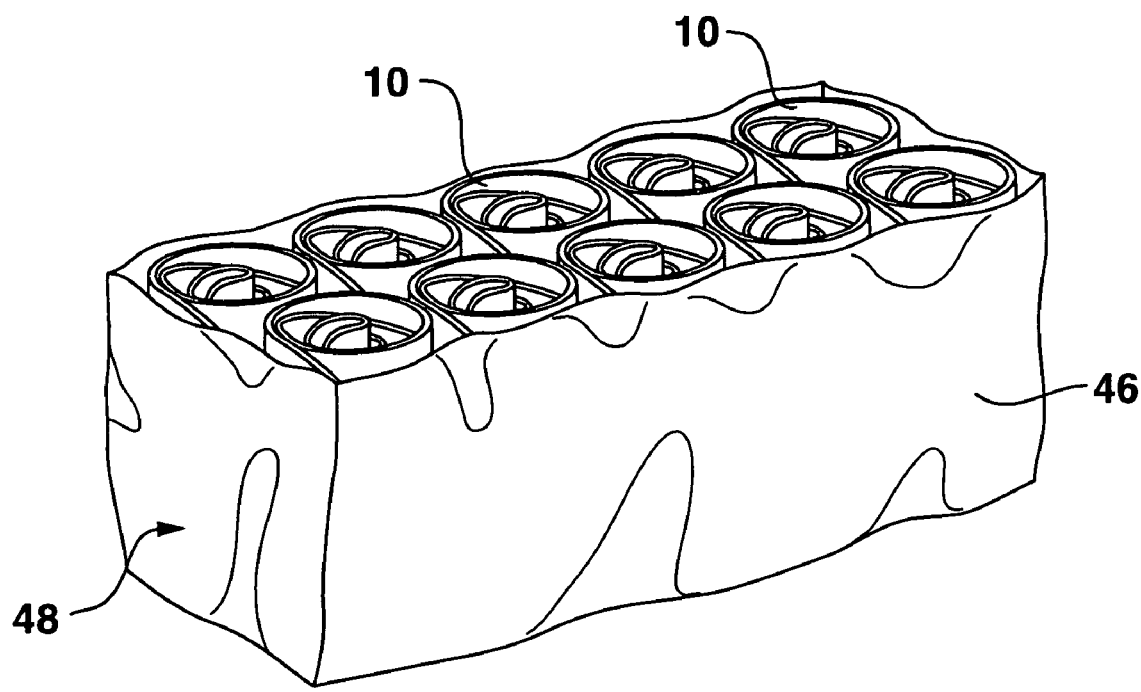
FIG. 7 is a perspective view of a package of rolled articles according to the invention.

Once rolled, the articles 10 may be packaged in various ways. As illustrated in FIG. 7, the articles 10 may be packaged directly with any conventional soft-side (i.e., plastic or film) or rigid (i.e., paperboard) packaging material 46 to form a package 48 of rolled articles 10. The articles 10 may be oriented in any desired manner in the package 48.

Figure 5B:
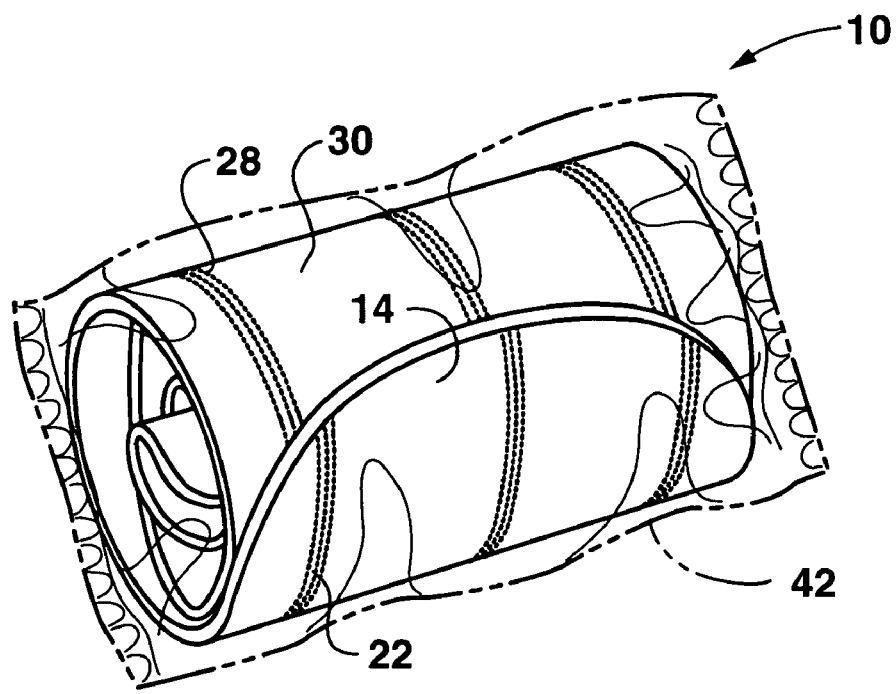
FIG. 5B is a perspective view of the article of FIG. 5A after being rolled and wrapped in an individual wrapper.

In may also be desired to individually wrap the articles 10 with any conventional wrapping material 42, as illustrated in FIGS. 3B and 5B prior to packaging the articles 10. The individual wrapper 42 may also be used by the consumer to dispose of soiled articles.

Articles 10 according to the invention also provide a means to discretely dispose of soiled articles without the need for disposal wrappers, pouches, or the like. After removing the article 10 from the undergarment, the wearer can simply grasp the edges of the article 10 and roll it such that the baffle 14 is outwardly facing. The soiled top cover 12 is thus not visible and the article will hold this rolled configuration without additional adhesives or the like for subsequent disposal. If desired, the rolled soiled article 10 may also be wrapped by the backing sheet removed from a clean article prior to subsequent disposal of the soiled article for additional odor protection.

Figure 8:
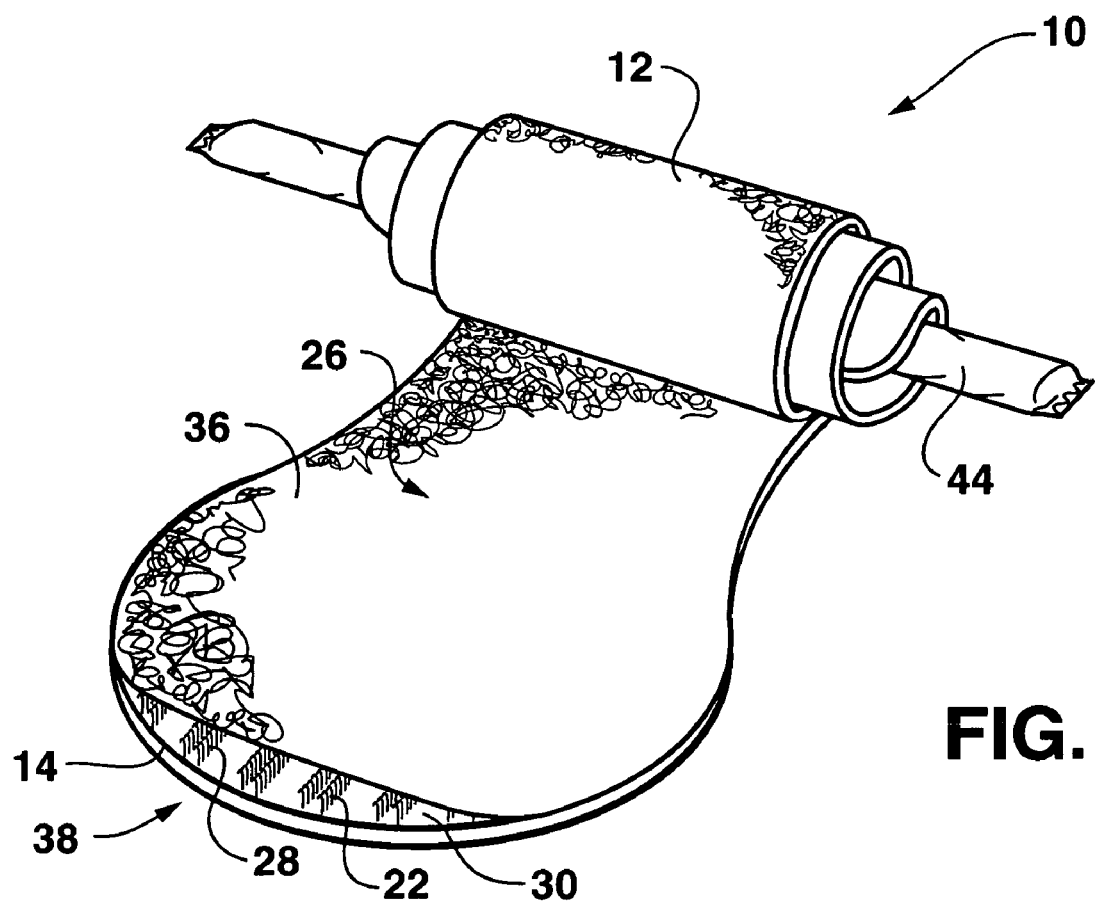
FIG. 8 is a perspective view of the embodiment according to FIG. 4 being rolled with an additional personal care absorbent article.

Referring to FIG. 8, the rolled tube-like configuration of the article 10 also provides a convenient and efficient means to include an additional personal care device 44, such as any conventional vaginal insert device, including tampons, interlabial devices, and so forth, with each article 10. Thus a protection system of two articles is provided to the consumer is a discrete and compact package. The additional device 44 may be separately wrapped so that if the device is not needed, the consumer may simply store it for later use.

It should be appreciated by those skilled in the art that various modifications and variations can be made to the embodiments of the absorbent article described herein without departing from the scope and spirit of the invention as set forth in the appended claims and equivalents thereof.

What is claimed is:

1. A rolled absorbent article for placement in the crotch region of an undergarment, comprising:
   a generally liquid permeable top cover;
   a generally liquid impermeable baffle having a garment facing side;
   an absorbent structure disposed between said top cover and said baffle;
   said garment facing side of said baffle comprising hook material defined in a pattern on the surface thereof, said hook material providing a primary attachment mechanism between said baffle and the undergarment;

said top cover comprising a hook compatible material that is releasably attachable to said hook material on said garment facing side of said baffle;

said article rolled into a tube-like configuration; and a protective backing sheet disposed between said top cover and said garment facing side of said baffle in said rolled configuration of said article, said backing sheet having at least one dimension that is less than a corresponding dimension of said article such that a limited portion of said top cover hook compatible material is releasably engaged by said hook material for maintaining said article in said rolled configuration.

2. The absorbent article as in claim 1, wherein between about 75% to about 95% of the surface area of said top cover is protected by said backing sheet from engagement with said hook material.

3. The absorbent article as in claim 1, wherein said protective backing sheet is a hook compatible material and is disposed against said garment facing side of said baffle prior to rolling said article.

4. The absorbent article as in claim 3, wherein said protective backing sheet comprises a nonwoven material.

5. The absorbent article as in claim 1, wherein said protective backing sheet is a poly film material that is not attachable to said hook material.

6. The absorbent article as in claim 1, wherein said protective backing sheet is shorter than said top cover in a longitudinal direction of said article and is disposed such that a single longitudinal edge portion of said top cover is exposed for engagement with said hook material.

7. The absorbent article as in claim 1, wherein said protective backing sheet comprises a shape and is disposed such that a border of said top cover is exposed around a perimeter of said protective backing sheet.

8. The absorbent article as in claim 1, wherein said protective backing sheet is disposed against said top cover prior to rolling said article.

9. The absorbent article as in claim 1, wherein said article is rolled from one longitudinal end thereof towards an opposite longitudinal end, said exposed portion of said top cover defined at said opposite longitudinal end.

10. The absorbent article as in claim 1, wherein said article is rolled from one lateral side thereof towards an opposite lateral side, said exposed portion of said top cover defined at said opposite lateral side.

11. The absorbent article as in claim 1, wherein said article is wrapped in a wrapping material.

12. The absorbent article as in claim 1, wherein said article is rolled such that said baffle is outwardly facing.

13. The absorbent article as in claim 12, wherein said protective backing sheet is also outwardly facing.

14. The absorbent article as in claim 1, wherein said article is rolled such that said top cover is outwardly facing.

15. The absorbent article as in claim 1, wherein said pattern of hook material comprises longitudinally disposed stripes of said hook material.

16. The absorbent article as in claim 15, wherein said stripes of said hook material have a width of about one-half of a distance between adjacent said stripes.

17. The absorbent article as in claim 1, wherein said hook material is defined on between about 25% to about 50% of a total surface area of said garment facing side of said baffle such that at least about 50% of said baffle is vapor permeable and said hook material is provided in an amount and placed to ensure that said hook material securely attaches said article to a wearer's undergarment.

18. The absorbent article as in claim 17, wherein hook material is defined in a pattern on said baffle to create a generally uniform vapor permeability profile over the surface area thereof.

19. The absorbent article as in claim 18, wherein said hook material is defined in a pattern of spaced longitudinal stripes.

20. The absorbent article as in claim 1, wherein said hook material is defined in generally continuous regions extending from one lateral side or longitudinal end of said article to an opposite respective lateral side or longitudinal end.

21. The absorbent article as in claim 1, wherein said hook material is defined in generally discontinuous regions.

22. The absorbent article as in claim 1, wherein said hook compatible material of said top cover comprises a liquid permeable nonwoven material.

23. The absorbent article as in claim 1, wherein said baffle comprises a base material with said hook material laminated directly onto said base material.

24. The absorbent article as in claim 1, wherein said article is one of a sanitary napkin, panty liner, and adult incontinent article.

25. The absorbent article as in claim 1, further comprising an additional personal care absorbent device rolled into said article.

26. The absorbent article as in claim 25, wherein said additional personal care absorbent device comprises a vaginal insert device.

27. An absorbent article for placement in the crotch region of an undergarment, comprising:

a generally liquid permeable top cover;

a generally liquid impermeable and vapor permeable baffle having a garment facing side;

an absorbent structure disposed between said top cover and said baffle; said garment facing side of said baffle comprising a hook material in a pattern such that said hook material provides a sole attachment mechanism between said baffle and the undergarment;

said top cover comprising a hook compatible material that is releasably attachable to said hook material on said garment facing side of said baffle; and a hook compatible protective backing sheet releasably attached to said garment facing side of said baffle, said protective backing sheet having at least one dimension that is less than a corresponding dimension of said baffle such that at least a portion of said hook material is exposed along at least one edge of said garment facing side of said baffle.

28. The absorbent article as in claim 27, wherein said protective backing sheet generally overlies said garment facing side of said baffle except for an exposed region at one longitudinal end of said baffle.

29. The absorbent article as in claim 27, wherein said protective backing sheet generally overlies said garment facing side of said baffle except for an exposed circumferential region around said backing sheet.

30. The absorbent article as in claim 27, wherein said protective backing sheet is a nonwoven material.

31. The absorbent article as in claim 27, wherein said hook material is defined in a pattern on said garment facing side of said baffle such that a generally uniform vapor permeability profile is established over the surface area of said baffle garment facing side.

32. The absorbent article as in claim 31, wherein said pattern of hook material comprises longitudinally disposed stripes of said hook material.

33. The absorbent article as in claim 32, wherein said stripes of said hook material have a width of about one-half of a distance between adjacent said stripes.

34. The absorbent article as in claim 31, wherein said hook material is defined on about 25% of a total surface area of said baffle garment facing side.

35. A method for packaging absorbent articles intended for placement in the crotch region of an undergarment, the absorbent article having a baffle with hook material provided on a garment facing side thereof, and a top cover formed of a hook compatible material, said method comprising placing a protective backing sheet against one of the top cover and garment facing side of the baffle and rolling the article into a tube-like configuration; the protective backing sheet having a size and configuration such that at least a portion of the hook material releasably engages with a portion of the top cover to maintain the article in the rolled tube-like configuration.

36. The method as in claim 35, further comprising wrapping the rolled article in an individual wrapper.

37. The method as in claim 35, further comprising forming a plurality of the rolled articles into a package of the articles.

38. The method as in claim 35, comprising placing the protective backing sheet against the garment facing side of the baffle prior to said rolling such that a portion of the hook material at a first longitudinal end of the article is exposed, and rolling the article from the opposite longitudinal end towards the first longitudinal end.

39. The method as in claim 35, comprising placing the protective backing sheet against the garment facing side of the baffle prior to said rolling such that a portion of the hook material at a first lateral side of the article is exposed, and rolling the article from the opposite lateral side towards the first lateral side.

40. The method as in claim 35, further comprising placing an additional absorbent device in article prior to rolling the article into the tube-like configuration.

41. The method as in claim 35, comprising rolling the article in a direction such that the baffle and protective backing sheet are outwardly facing.

* * * * *